United States Patent [19]

Giampapa

[11] Patent Number: 5,137,533
[45] Date of Patent: Aug. 11, 1992

[54] HAIR IMPLANTATION STRUCTURE

[76] Inventor: Vincent C. Giampapa, 89 Valley Rd., Montclair, N.J. 07042

[21] Appl. No.: 796,376

[22] Filed: Nov. 22, 1991

Related U.S. Application Data

[63] Continuation-in-part of Ser. No. 464,311, Jan. 12, 1990, which is a continuation-in-part of Ser. No. 290,712, Dec. 27, 1988, abandoned.

[51] Int. Cl.⁵ .............................................. A61F 2/10
[52] U.S. Cl. ..................................................... 623/15
[58] Field of Search ........................................... 623/15

[56] References Cited

U.S. PATENT DOCUMENTS 4,969,903 11/1990 Valle ...................................... 623/15

FOREIGN PATENT DOCUMENTS 2372621 8/1978 France ................................... 623/15

Primary Examiner—David Isabella
Assistant Examiner—Debra S. Brittingham
Attorney, Agent, or Firm—Melvin K. Silverman

[57] ABSTRACT

A structure for implantation below the surface of the epidermis of the scalp includes a group of human hair shafts embedded within a non-hydrophilic core. The core is surrounded by a cylindrical annulus of hydrophilic material which possesses a property of volumetric expansion of at least two fold after fixation within the human scalp. Through such expansion an artificial arch or within the scalp is obtained.

8 Claims, 4 Drawing Sheets

HAIR IMPLANTATION STRUCTURE

REFERENCE TO RELATED APPLICATION

This case is a continuation-in-part of application Ser. No. 07/464,311, filed Jan. 12, 1990, which is a continuation-in-part of application Ser. No. 290,712 filed Dec. 27, 1988 now abandoned.

BACKGROUND OF THE INVENTION

The present invention relates to a hair implant structure adapted for implantation within the epidermis and dermis of the scalp and, further, relates to a surgical method adapted for the use of the present inventive implant structure.

The most pertinent prior art known to the inventor comprises U.S. Pat. No. 3,842,439 (1974) to Connelly, entitled Method of Replacing Hair; U.S. Pat. No. 3,914,801 (1975) to Dick, entitled Method of Applying Hair; U.S. Pat. No. 4,517,997 (1985) to Forchetti, entitled Hair Implant Structure; U.S. Pat. No. 3,003,155 to Mielzenski, entitled Hair Darts, and U.S. Pat. No. 4,776,337 to Palmez, entitled Expandable Graft.

The above reference to Connelly teaches the use of a continuous suture and the attachment thereto of linear wefts of hair, either natural or synthetic. The above reference to Dick also makes use of a suture employing, particularly, an inert material such as silicone as the suture material. Also, use is made of a specially configured suture needle to practice the invention of Dick.

The above reference to Forchetti makes use of an artificial root structure applied to the individual hair filaments and involves the implantation of one filament at a time into the scalp. As respects the concept of the use of an artificial root, Forchetti reflects the most pertinent prior art known to the inventor.

As may be noted by a review of the above references, the prior art approaches to surgical hair replacement have involved the use of a large number of sutures and incisions, as well as the use of special purpose instrument to achieve the desired end. Even with such special surgical instruments and techniques, the provision of a safe and durable method of surgical hair implantation has eluded prior art efforts in the area. Accordingly, it is to this long-felt need in the prior art that the instant invention is directed.

SUMMARY OF THE INVENTION

The invention constitutes a hair implant structure adapted for implantation below the surface of the epidermis of the scalp. The structure, more particularly, comprises a multiplicity of human hair shafts, said multiplicity comprising a group of said such shafts, said groups embedded in a core of substantially non-hydrophilic material. An annulus of hydrophilic material complementally surrounds said non-hydrophilic core. Said hydrophilic annulus possesses properties of hydrophilic expansion of at least two fold such that, subsequent to implantation within the scalp, absorption of water from body tissues will effect an expansion of said annulus thereby anchoring the peripheral surface thereof within the epidermis and dermis of the scalp. The human hair shafts may be provided with a coating of silicone.

It is an object of the present invention to provide an improved hair implantation structure of the type above set forth.

It is another object of the invention to provide a novel hair implant structure suitable for firm and secure implantation within the epidermis of the human scalp without causing rejection thereof by the surrounding tissue.

It is a further object to provide a hair implant structure suitable for implant in living skin, which includes an artificial root structure with which the subcutaneous tissue of the epidermis, as well as other tissue therein, will interact in a natural and durable fashion.

The above objects and yet other objects and advantages of the present invention will become apparent from the hereinafter set forth Detailed Description of the Invention, the Drawings, and claims appended herewith.

DETAILED DESCRIPTION OF THE INVENTION

Figure 2:
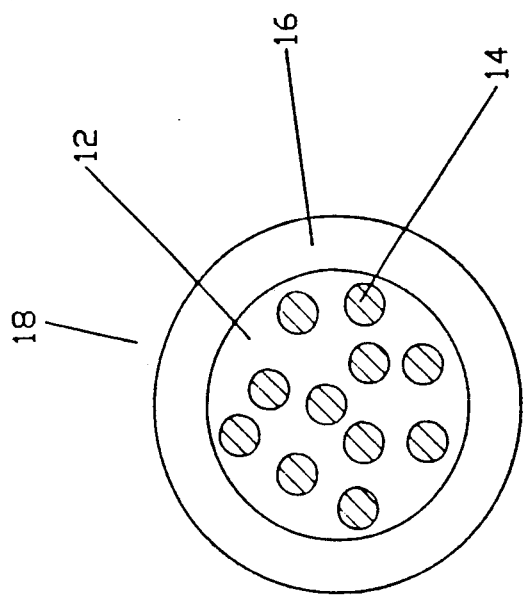
FIG. 2 is an axial cross-sectional schematic view taken along Line 2—2 of FIG. 1.
Figure 1:
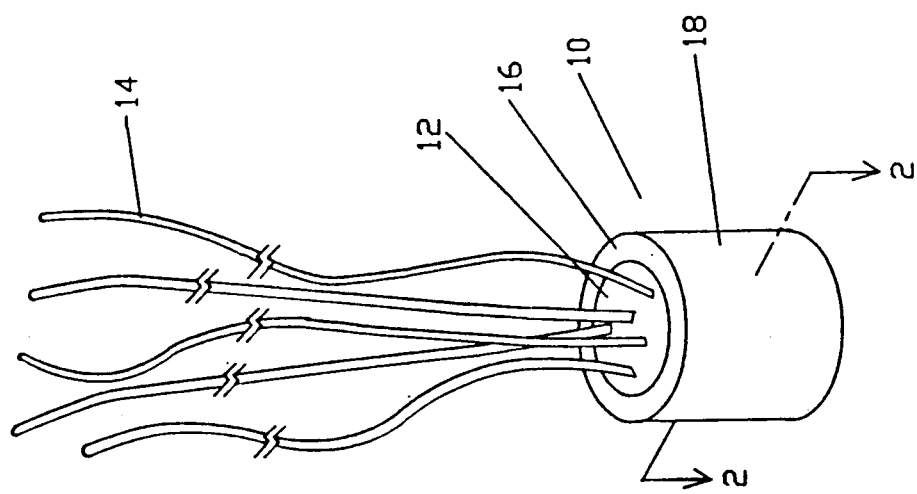
FIG. 1 is a schematic view of a hair packet implantation structure constructed in accordance with the present invention.

In FIG. 1 there is shown an inner core 12 including a multiplicity of human hair shafts 14. Said core 12 is formed of a substantially non-hydrophilic material such as silicone. The essential property of the core is that it will not swell or expand in the presence of water or moisture. A representational diameter of the inner core 12 is about one millimeter. It is noted that said core may assume a number of geometrics including cylindrical and ellipsoidal geometries.

Each of said shafts 14, including the roots 15 thereof, may be removed in groups from a donor area of the human scalp, such as the back of the patient's head. Alternatively, the hair shafts may be obtained from a non-patient donor, either with or without roots. Each of the hair shafts may then be coated with a fine layer of silicone or polytetraflouorethylene. Thereafter the shafts are embedded within the core material to form core 12.

Figure 3:
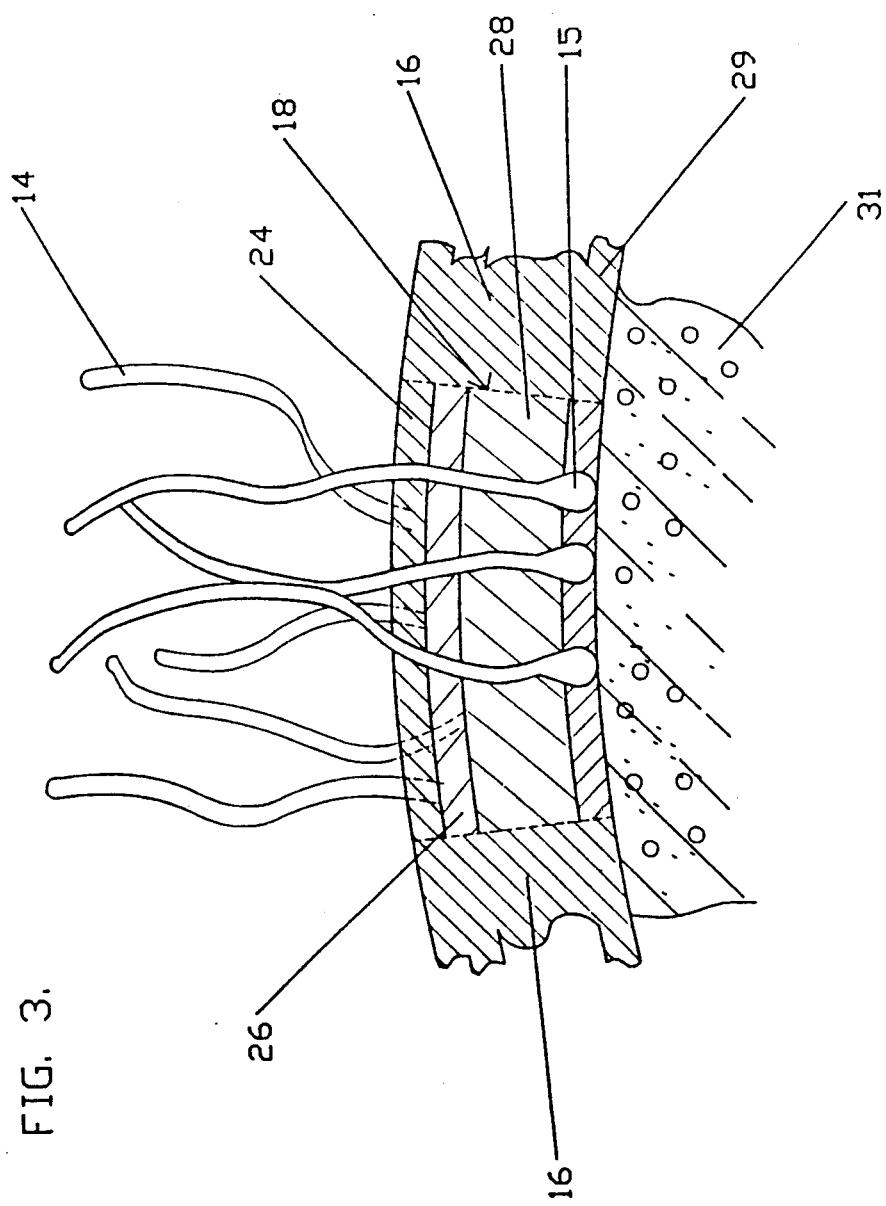
FIG. 3 is a radial cross-sectional schematic view of the implantation structure after implantation into the epidermis according to a first method of implantation.
Figure 5:
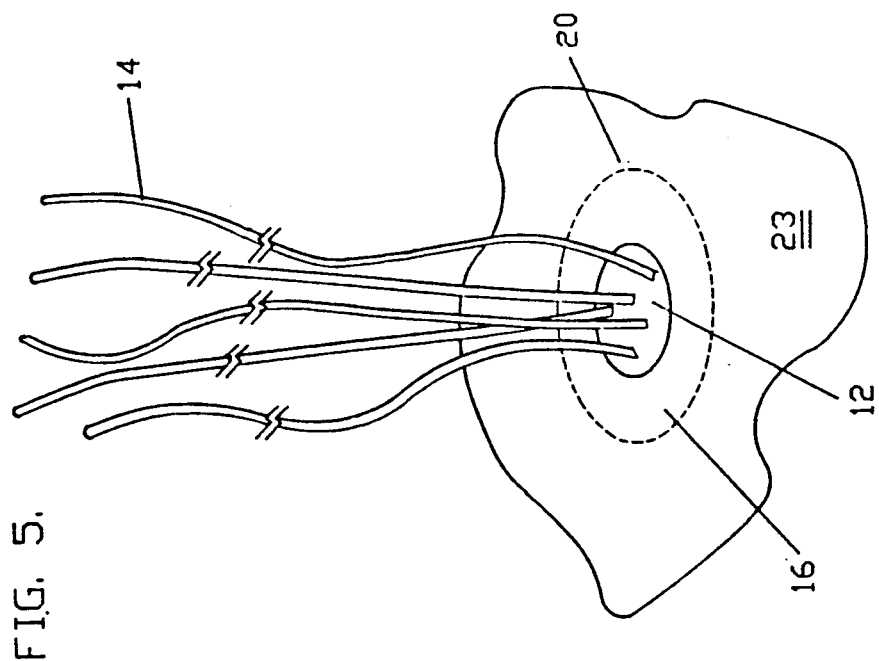
FIG. 5 is an external perspective view of the hair implantation structure after implantation into the scalp.

The core 12 is thereafter surrounded by an annulus 16 of hydrophilic material which complementally surrounds said core 12. A peripheral interface 18 between core 12 and annulus 16 may be achieved by a pressure bond therebetween. The hydrophilic annulus may be formed of material such as poly-2-hydroxy-ethylmethacrylate which possesses properties of absorption of water or moisture. As a result of such properties of absorption the annulus 16 will, after implantation beneath the epidermis, swell or expand to two or three times its volume (See FIG. 5). Such expansion performs the function of improving the fixation of the outer surface 18 of the annulus 16 to the wall of an incision 20 and the various layers of the skin between the epidermis 23 and the skull 31. More particularly, with reference to the enlarged schematic view of FIG. 3, it may be noted that the entire structure may, by suitable surgical technique, be implanted into the scalp at the level of the galea 29 which surrounds the skull 31. Accordingly, the insertion necessary to implant the inventive structure 10 requires the surgical incision 20 into the epidermis 23 of the scalp. The epidermis includes subcutaneous layers above said galea 29 and particularly layers know as the stratum corneum 24, the stratum germinativum 26 and the corium (also known as the dermis) 28.

Figure 4:
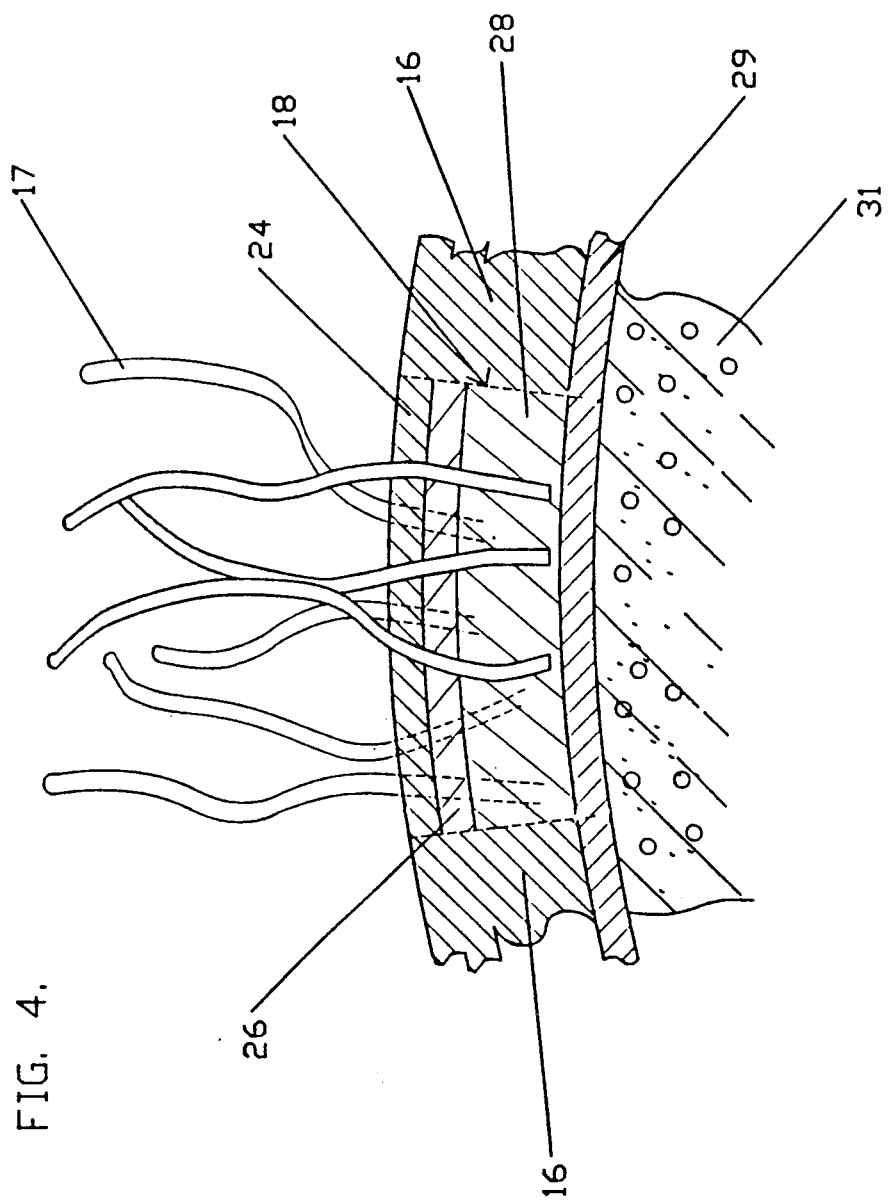
FIG. 4 is a view similar to FIG. 3, however showing the implanted structure according to a second surgical method.

With reference to FIG. 4, there is shown an embodiment of the instant invention in which hair shafts 17 are used which have been cut from a non-patient donor's hair without the removal of the root from the donor and, further, in which the implantation structure 10 has been implanted only to the bottom of the corium 28. It is, however, to be appreciated that the non-hydrophilic core 12 (which is shown in cross-section in the views of FIGS. 3 and 4) may, according to the discretion of the physician, be embedded either to the level of the corneum 28 or galea 29.

Figure 6:
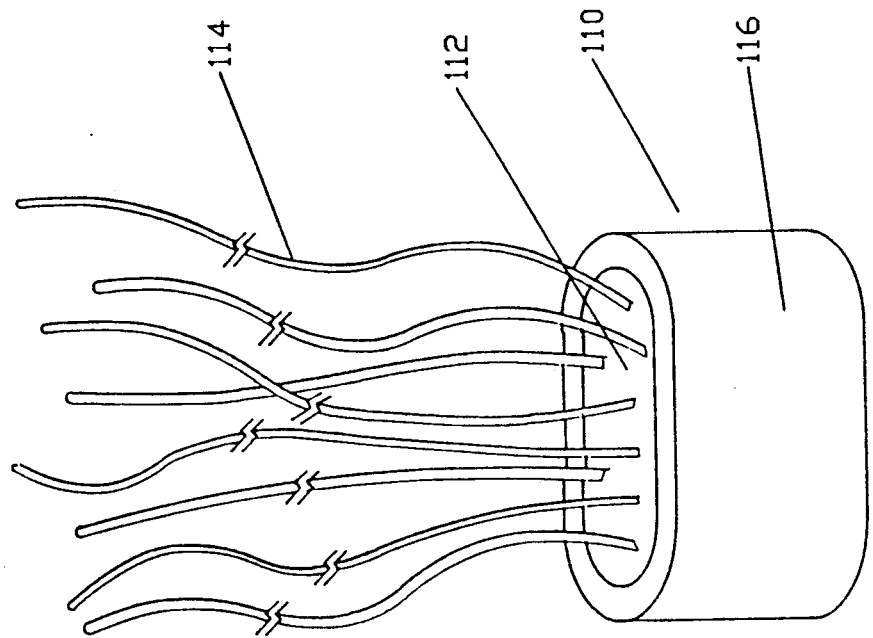
FIG. 6 is a perspective schematic view of the hair implantation structure constructed in accordance with a second embodiment of the present invention.

With reference to the view of FIG. 6, it is seen that the present inventive implantation structure may be provided with an essentially elliptical geometry in which inner core 112 comprises an elliptical cylinder and annulus 116 comprises an elliptical annuloid. In this embodiment, the length of the major axis of annulus 116 will be between 4 and 5 millimeters.

In the practice of the present invention, it has been found that permanent fixation of peripheral surface 18 to incision 20 will occur within ten days of the original insertion. During this period the volume of annulii 16 and 116 will, as above noted, increase in volume by between two and three times thereby assuring permanent fixation of surface 18 within the epidermis 23 of the scalp.

Each of shafts 14, 17, and 114 will, in a preferred embodiment, be coated with a thin layer of silicone or polytetraflouroethylene prior to placement within core 12 or 112. The purpose of such coating is to protect the shafts from an immunologic response process known as foreign protein reaction. This process will, in the absence of a suitable protective coating, dissolve the hair shafts and cause inflammation of the skin and scalp.

It is to be noted the use of sutures in the surgical implantation of structure 10 into the scalp is optional and, whether or not sutures are employed, a suitable tension will exist between the walls of the epidermis and the surface 18 of the implantation structure 10.

In view of the above, there is, accordingly, provided a hair implantation structure and method having an artificial anchor which will remain secured, for an indefinite period within the human scalp.

To simulate a natural head of hair, it will of course be necessary to implant many packets of hair shafts of the type above described. However, it has been found the number of such hair implantation structures are substantially less than is the case in other methods of implantation because, among other reasons, the herein structure permits the creation of patterns having a lesser number of individual incisions than is the case in prior art efforts of the present type. Further, the instant method does not rely upon the existing blood supply of the scalp as in the case with prior art hair plugs or grafts. Accordingly, the instant method is ideal for hair and scalp re-construction in traumatized or burn situations, as well as in cosmetic applications.

It is to be appreciated that while there has been shown and described the preferred embodiment of the present invention, the invention may be embodied otherwise that is herein specifically illustrated and described and that, within said embodiment, certain change in the detail and construction, in the form and arrangement of the parts may be made without departing from the underlying idea of principles of this invention within the scope of the claims appended herewith.

Having thus described my invention, what I claim as new, useful and non-obvious and, accordingly, secure by Letters Patent of the United States is:

1. A hair implantation structure for insertion below the surface of the epidermis of the scalp, the structure comprising:
    (a) a multiplicity of human hair shafts, said shafts embedded in a core of substantially non-hydrophilic material; and
    (b) an annulus of tissue-compatible hydrophilic material having an outer surface surrounding said non-hydrophilic core, said hydrophilic annulus having a property of hydrophilic volumetric expansion of at least two fold,
        whereby, upon implantation of said structure within the human scalp, fixation of the outer surface of said hydrophilic annulus will be effected by the expansion of the tissue-compatible material of said annulus.

2. The structure as recited in claim 1 in which said core comprises cylindrical core.

3. The structure as recited in claim 1 in which said core comprises elliptical core.

4. The structure as recited in claim 1 in which said core comprises silicone and in which said annulus comprises poly-2-hydroxy ethylmethylacrate.

5. The structure as recited in claim 1 in which said human hair filaments are provided with a coating of silicone prior to embedding in said core.

6. The structure as recited in claim 1 in which said multiplicity of hair shafts are taken from the scalp of a patient.

7. The structure as recited in claim 1 further comprising a pressure bond between said core and said annulus.

8. The structure as recited in claim 6, further comprising a pressure bond between said core and said annulus.

* * * * *